United States Patent [19]

Woodbury et al.

[11] Patent Number: 5,235,089

[45] Date of Patent: Aug. 10, 1993

[54] PROCESS FOR THE PREPARATION OF 3-CYANO-3,5,5-TRIMETHYLCYCLOHEXANONE

[75] Inventors: Richard P. Woodbury, Amherst; Jon C. Thunberg, Milford; Steven P. VanKouwenberg, Auburn, all of N.H.; Walter B. Begonis, Reading, Mass.

[73] Assignee: Hampshire Chemical Corp., Lexington, Mass.

[21] Appl. No.: 843,867

[22] Filed: Feb. 27, 1992

[51] Int. Cl.$^5$ .................................................. C07C 253/10
[52] U.S. Cl. ..................................... 558/341; 558/351
[58] Field of Search ........................................... 558/341

[56] References Cited

U.S. PATENT DOCUMENTS

| | | | |
|---|---|---|---|
| 4,299,775 | 11/1981 | Dubreux | 260/464 |
| 5,011,968 | 4/1991 | Thunberg et al. | 558/341 |
| 5,091,554 | 2/1992 | Huthmacher et al. | 558/341 |
| 5,142,090 | 8/1992 | Pontoglio et al. | 558/341 |

FOREIGN PATENT DOCUMENTS

| | | |
|---|---|---|
| 0275204 | 4/1964 | Australia . |
| 0028179 | 5/1981 | European Pat. Off. . |
| 0425806 | 9/1990 | European Pat. Off. . |
| 0433615 | 10/1990 | European Pat. Off. . |
| 1083871 | 5/1958 | Fed. Rep. of Germany . |
| 1240854 | 5/1967 | Fed. Rep. of Germany . |
| 3640306 | 6/1988 | Fed. Rep. of Germany . |
| 1452374 | 8/1966 | France . |
| 116038 | 7/1982 | Japan . |

OTHER PUBLICATIONS

Du Pont Material Safety Data Sheet (Apr. 20, 1990).
Chemical Abstracts 60:11885e, W. Kenneth Musker (1964).
Chemical Abstracts 103:75809z, Sumitomo Chemical Co., Ltd. (1985).

*Primary Examiner*—Joseph Paul Brust
*Attorney, Agent, or Firm*—Nields & Lemack

[57] ABSTRACT

A process for the preparation of isophorone nitrile utilizing solutions of lithium hydroxide or lithium cyanide, solid LiOH or solid LiOH•H$_2$O as a catalyst. The reaction is carried out under precisely controlled temperature conditions and cyanide feed rate profiles to maintain a reasonably constant concentration of non-reacted cyanide, thereby minimizing the formation of undesirable diisophorone, its nitrile derivative(s) and HCN polymers. A polyacidic acid can be used to acidify the batch, followed by filtration to remove the precipitated lithium salt of the acid, and vacuum distillation to remove liberated HCN and excess isophorone. The resulting isophorone nitrile is obtained in high yield and with low impurity content.

28 Claims, 2 Drawing Sheets

PROCESS FOR THE PREPARATION OF 3-CYANO-3,5,5-TRIMETHYLCYCLOHEXANONE

BACKGROUND OF THE INVENTION

Isophorone nitrile (IPN) or 3-cyano-3,5,5-trimethylcyclohexanone is a critical intermediate in the synthetic scheme to the diamine (IPDA) and finally to the diisocyanate (IPDI). Numerous prior art processes have been developed to synthesize IPN. For example, U.S. Pat. No. 4,299,775 to Dubreux discloses a two-phase process for the preparation of IPN by reacting isophorone (IPH) with a cyanide in the presence of a catalytic amount of a phase-transfer agent. The quaternary ammonium catalysts are used as their chloride or bromide salts; the chloride ion or bromide ion is exchanged for cyanide ion and this cyanide ion is transferred from the water to the solvent layer via the well known phase transfer mechanism.

German Patent No. 1,240,854 to Scholven-Chemie discloses a process for the preparation of IPN by reacting isophorone with hydrogen cyanide in the presence of a basic catalyst such as alkali cyanide, hydroxides or alcoholates. The catalyst is removed by washing with dilute nitric acid.

Japanese Laid-Open specification 61-33157 to Nippon Kagako K.K. discloses a process for the preparation of isophorone nitrile by reacting isophorone with hydrogen cyanide in the presence of tetra-n-butylammonium hydroxide, tetra-n-butylphosphonium hydroxide or benzyltrimethylammonium hydroxide. The resulting reaction liquid is washed with water.

However, acidic washing to remove catalyst produces an aqueous effluent saturated in isophorone and containing some cyanide. Disposal of such an effluent adds significantly to the cost of the product.

European Patent Application 0 433 615 discloses a method for producing 1,3,3-trimethyl-5-oxo-cyclohexane-carbonitrile by the addition of hydrogen cyanide to isophorone in the presence of lithium hydroxide as a catalyst, at temperature conditions of 100° to 160° C. U.S. Pat. No. 5,011,968 discloses a process for producing isophorone nitrile in the presence of a quaternary ammonium hydroxide as a catalyst.

Many of the conventional catalysts, and in particular, amine-generating catalysts, used in the isophorone nitrile production can poison the metal catalysts used in the subsequent hydrogenation of isophorone nitrile to IPDA, thereby significantly reducing catalyst life. It is therefore advantageous and often necessary to eliminate such catalysts from the product, such as by distillation. However, such additional process steps are labor intensive and costly. In addition, important by-products of the base-catalyzed reaction of HCN and IPH include diisophorone (dimer) and its conversion to cyano derivatives. For example, as described in the Journal of Organic Chemistry, 42, (9), 1600-1607 (1977), the following reactions can occur:

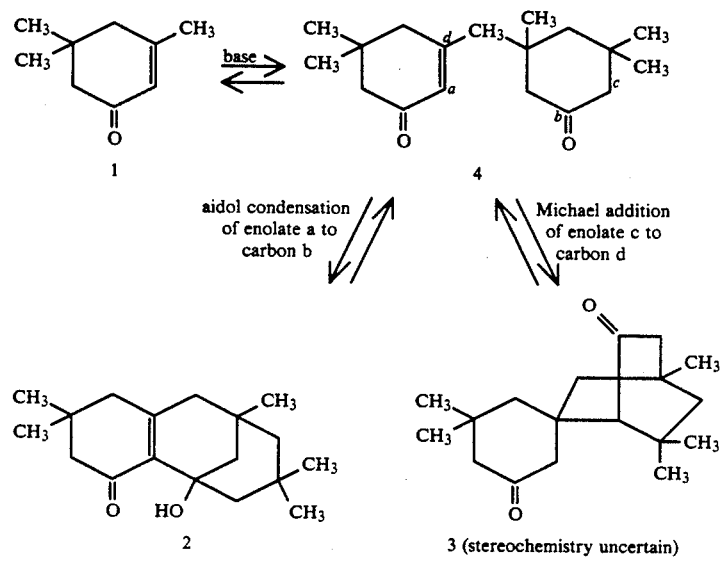

Isophorone itself contains many impurities. Upon exposure to air, the product becomes yellow, which is believed to be a result of the apparent oxidation product of isophorone via direct addition of oxygen to the unsaturated site:

Thus, it is also advantageous to minimize the formation of such impurities, of diisophorone, and of its HCN adducts. In addition, elimination of residual HCN and excess IPH from the resulting product is necessary.

SUMMARY OF THE INVENTION

The problems of the prior art have been solved by the instant invention, which provides a process for the preparation of isophorone nitrile utilizing lithium hydroxide, lithium hydroxide monohydrate, lithium cyanide, or solutions thereof, as a catalyst in accordance with the following reaction:

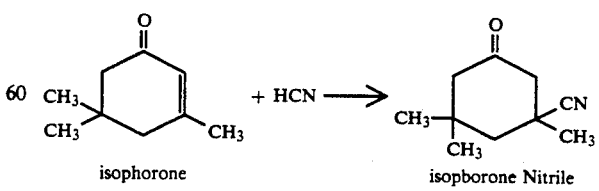

By carrying out the foregoing reaction under precisely controlled catalyst concentration, temperature conditions, and cyanide feed profiles, to maintain a reasonably constant concentration of non-reacted cyanide, the formation of undesirable diisophorone and its nitrile derivative(s) is minimized. A polyacidic acid can be used to acidify the batch, followed by filtration to remove the precipitated lithium salt of the acid, and vacuum distillation to remove liberated HCN and excess isophorone. The resulting isophorone nitrile is obtained in high yield and with low impurity content, and light color.

DETAILED DESCRIPTION OF THE INVENTION

Figure 1:
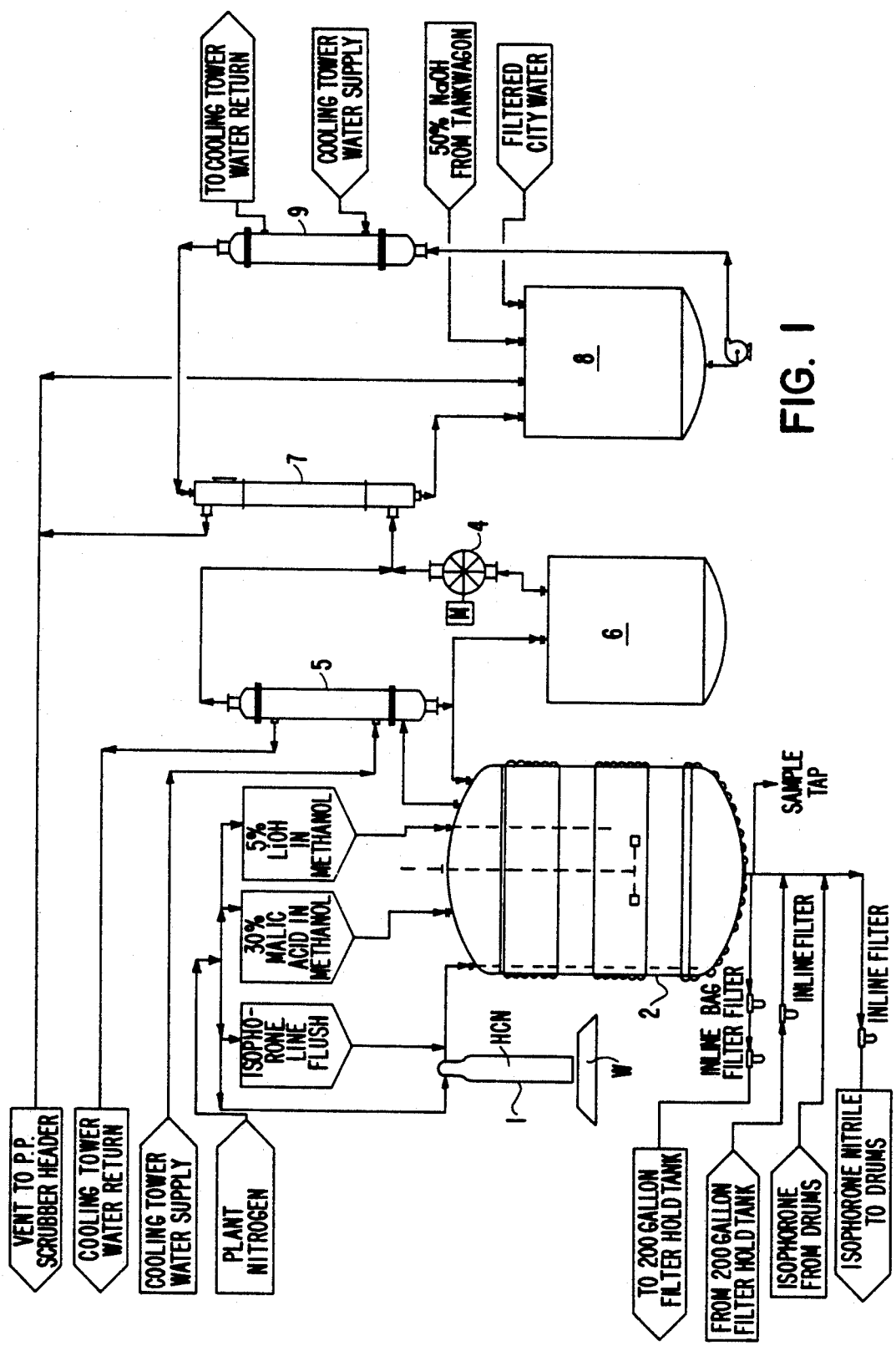
FIG. 1 is a diagram illustrating the process in accordance with the present invention.

In accordance with the process of the present invention, which has as an object the preparation of isophorone nitrile in high yield and with low impurity content, free cyanide must be present at all times but in low concentration in order to prevent the generation of free LiOH, which results in the undesirable formation of diisophorone and leads to formation of diisophorone nitrile(s) and other high boilers. If the free cyanide concentration drops below a level equivalent to the amount of catalyst present (about 200 ppm) at any time during the reaction, diisophorone and diisophorone nitrile(s) begin to form. On the other hand, if the free cyanide concentration exceeds about 4000 ppm, dark and turbid product is produced. It is believed that this is due to the formation of cyanide polymer. Any reaction temperature profile, coupled with an optimized HCN feed profile which will maintain a free HCN concentration of about 200 to about 4000 ppm, preferably of about 500 to about 2000 ppm throughout the reaction, will produce excellent product. In the preferred embodiment of the instant invention, HCN addition is begun and the basic catalyst is immediately added to the reaction system at a low temperature. The temperature is then increased at a controlled rate while feeding the HCN also at a controlled rate. By starting the HCN feed prior to adding the catalyst, LiCN is formed without ever exposing the IPH to LiOH. This minimizes dimerization and the formation of high boilers. A suitable low temperature at which the catalyst is introduced is 80° C. The temperature of the reaction system may then be ramped to, for example, 110° C., either by the independent addition of heat, or by using the heat of reaction, or by a combination of the two. The temperature is maintained at about 110° C. for the balance of the reaction. It is important to maintain the free HCN at a low concentration to minimize the formation of HCN polymer. Since the IPH concentration is highest at the start of the HCN feed and decreases throughout the run, HCN consumption may be moderated by using a temperature profile with a reduced temperature at the start and increasing the temperature as the IPN formation rate decreases. Alternatively, both the rate of HCN addition and the temperature can be simultaneously controlled in such a way that a nearly constant concentration of HCN is maintained.

The present inventors have found that the generation of diisophorone by addition of LiOH to isophorone does not occur during short exposure below temperatures of about 90° C. Accordingly, the reaction can be conducted in the presence of catalyst at temperatures below about 90° C. to accomplish the same object.

The quality of the isophorone and the concentration of the lithium catalyst are important factors that must be addressed in order to obtain the product in good yield. Isophorone which has a yellow color and a high acidity does not produce good product. The exact effect of color is unknown, but high acidity tends to neutralize and thus destroy the catalyst. Accordingly, it is preferred that the isophorone be distilled prior to reaction with HCN. When good quality (i.e., low acidity) IPH is used, the proper mole ratio of Li:HCN is between about >0.0025:1.00 and less than about 0.01:1.00; preferably about 0.005–0.01:1.00, most preferably about 0.0075–0.0080:1.00, especially where non-distilled HCN is used. Such mole ratios ensure that sufficient cyanide concentration is present at all times for the addition of HCN to isophorone without the simultaneous presence of free base which would catalyze the undesirable formation of diisophorone from IPH. A mole ratio of 0.005:1.00 may produce low yields due to neutralization of some of the catalyst by acidity in the IPH plus acidity in the HCN; thus, if this mole ratio is employed, the HCN should be distilled prior to the reaction. A mole ratio greater than ~0.01:1.00 may cause dimerization of IPH to occur.

Significant amounts of water must be avoided, as its presence results in reduced yields and increased formation of high boilers; hence, the lithium catalyst should be added as a solid or as a solution in an organic solvent. Any solvent which will dissolve the LiOH•H$_2$O but is inert in the presence of LiOH is acceptable. (Water also could be used, but may cause somewhat reduced yields and increased by-product formation). Suitable solvents include acetone and dioxane, and alcohols such as methanol and ethanol. The preferred solvent is methanol.

To minimize the formation of high boilers (such as diisophorone and its cyano derivatives), the catalyst must be neutralized with an acid just at the point where the HCN has fully reacted, to eliminate cyanide ion, primarily in the form of LiCN, and free base (LiOH). Suitable acids for this purpose include polyacidic acids such as malic (hydroxysuccinic) acid, oxalic acid, sulfuric acid, and phosphoric acid, with malic acid being preferred. Malic acid is relatively inexpensive, is very soluble in water and in methanol, and forms a crystalline precipitate of the di-lithium salt which is easily removed by filtration, leaving a clear light yellow solution of IPN in IPH. Such solution leaves no residue upon distillation and will therefore not foul the packing in the stripper. Since methanolic solutions of malic acid are unstable (the mono and/or dimethyl ester of malic acid forms rapidly; the loss of titratable acidity at 25° C. being 25% after two days and 52% after two weeks), where methanolic solutions of malic acid are employed, such solutions should be freshly prepared. For this reason, aqueous solutions of malic acid are preferred over methanolic solutions thereof. In addition, with water as solvent, the particle size of the Li$_2$ malate is improved, resulting in rapid filtration. Aqueous solutions of malic acid, however, if not used soon after preparation, degrade due to bacterial action. For these reasons, we prefer to add malic acid as a solid. This avoids the problems associated with solutions and eliminates the solvent which must later be removed by nitrogen sparging (the condensate of isophorone/water/methanol cannot be recycled and thus becomes a waste). In contrast to malic acid, phosphoric acid forms LiH$_2$PO$_4$, which precipitates as a fine sticky solid which filters poorly. Preferably the acid is used in a mole ratio of 0.5-0.6M acid:1.00M lithium. The destruction of the catalyst halts any possibility of further dimerization of IPH and also decomposes the LiCN to HCN. The liberated HCN is removed during an IPH stripping operation.

A kinetic study was undertaken to determine whether there existed a temperature low enough to prevent LiOH from catalyzing the dimerization of isophorone but high enough to allow LiCN to form from LiOH and HCN and to catalyze the addition of HCN to IPH. In accordance with the preferred embodiment of the instant invention, it has been determined that LiOH can be added to isophorone at temperatures up to 80°-90° C. without generating impurities, provided that the HCN feed is promptly initiated. In addition, neutralizing the catalyst with malic acid rather than phosphoric acid improves the filtering process by forming easily filterable crystals in the IPN reaction matrix. The dilithium salt of malic acid is also insoluble in the isophorone. Lithium cyanide is the preferred catalyst. Where lithium hydroxide is used, it should be added as a solid or as a solution in an organic solvent, with the preferred solvent being methanol. Solid LiOH•$H_2O$ causes less diisophorone formation than LiOH in methanol, presumably because the former only slowly dissolves in IPH and therefore less is instantly available for catalysis of the dimerization of IPH. In addition, solid LiOH•$H_2O$ eliminates the addition of solvent which occurs when methanolic LiOH is used. Accordingly, solid LiOH•$H_2O$ is preferred over LiOH dissolved in a solvent. The mono-hydrate form is preferred over anhydrous LiOH for economic reasons.

Upon catalyst addition, suitable reaction temperatures are between about 80° and 115° C., preferably between about 110° and 115° C., most preferably about 110° C.

Turning now to FIG. 1, there is shown one example of apparatus to carry out one embodiment of the process of the instant invention. Isophorone is fed from a drum (not shown) to a 200 gallon stainless steel reactor 2. Liquid hydrogen cyanide is fed from pressurized cylinder 1 to reactor 2. 5% LiOH in methanol and 30% malic acid in methanol are added to reactor 2 as shown. When the reaction is finished, the crude product is passed through a filter to remove the dilithium malate precipitate. The filtered product is collected in a 200 gallon stainless steel hold tank (not shown). When filtration is complete, the filtered product is returned to reactor 2. Vacuum is pulled on reactor 2 by vacuum pump 4. Vapors are condensed in condenser 5 and the condensed vapors are collected in condensate receiver 6. Non-condensable vapors (such as HCN) are vented from vacuum pump 4 to scrubber 7. Dilute NaOH is circulated to scrubber 7 from scrubber hold tank 8 through condenser 9 which serves as a heat exchanger. The molten IPN product, which has been stripped free of IPH, methanol, and HCN, is transferred to drums.

EXAMPLE 1

The apparatus used included a 1 liter Parr autoclave/Harvard syringe pump. The batch charge was based upon the mole ratio of IPH:HCN of 2.00:1.00. This amount of IPH was needed to dissolve all the IPN formed. Use of less IPH would have resulted in crystallization during filtrations had the solution cooled to <~60° C. The actual charge was 4.00M IPH (553 grams at 99%) and 2.00M HCN (54.1 grams). Cyanide ion was determined by amperometric titration with standard $AgNO_3$ with the sample dissolved in 50/50 isopropanol/water solvent plus borax buffer. Acidity and pH were determined by dissolving the sample in 50/50 water/isopropanol. pH was measured using a 2% or 5% solution. Acidity or alkalinity was determined by titration with standard 0.1N NaOH or HCl to pH 7.0.

The Parr reactor was charged with IPH, the head space purged with $N_2$, and the IPH was heated to 80° C. LiCN catalyst was prepared by adding HCN to a solution of LiOH•$H_2O$ in methanol. This catalyst was added to the IPH and HCN was added immediately thereafter at a constant rate over 60 minutes while simultaneously and rapidly raising the temperature to 110° C. Samples were taken at 15 minute intervals and titrated for free HCN. The batch was held at 110° C. for various periods of time and samples were again taken during this hold. The data are given in Table 1:

TABLE I

| | Catalyst is LiCN (methanol + LiOH.H20 + HCN) | | | |
|---|---|---|---|---|
| | Expt. No. | | | |
| | 1 | 2 | 3 | 4 |
| Mole Ratio Li:HCN | 0.025 | 0.01 | 0.005 | 0.0025 |
| ppm HCN During Reaction, min/ppm | 15  6321<br>30  420<br>45  1529<br>60  818 | 15  2959<br>30  360<br>45  488<br>60  491 | 15  1136<br>30  295<br>45  1922<br>60  5308 | 15  1672<br>30  5838<br>45  19800<br>60  32300 |
| % Conversion HCN to IPN During Reaction | 93.2% | 99.0% | 91.6% | 64.2% |
| % Impurities in IPN/IPH Solution at End of HCN Feed | 0.10% | 2.60% | 0.80% | 0.00% |
| ppm HCN During Hold @ 110° C., hr or min/ppm | 1 hr  947<br>2 hr  620<br>3 hr  199 | 1 hr  480<br>2 hr  472<br>3 hr  220 | 30  291<br>—<br>— | 1 hr  20250<br>—<br>— |
| Final Product: % Conversion of HCN to IPN | 51.20% | 85.50% | 98.70% | n.d. |
| Final Product: % Impurities in IPN/IPN Solution | 5.10% | 8.40% | 0.80% | n.d. |

These data show the excellent results obtained when using an amount of catalyst in the range of 0.005-0.01 M/M HCN, and the severe decomposition of product occurring by heating the crude IPN in the presence of the catalyst.

EXAMPLE 2

The apparatus used included a 1 liter flask with a heating mantle and reflux condenser. Temperature was controlled by a Love Controller operating relays controlling the heat to the heating mantle and a ⅛" ss cooling coil mounted in the flask. HCN was added via the Harvard syringe pump used in Example 1. The batch charge was the same as in Example 1, except that the HCN was distilled to remove the acidity due to $H_2SO_4$ by adding 5% water thereto and pumping this HCN/$H_2O$ solution into a small heated tube. The HCN was flashed off and carried into and below the surface of the IPH via a continuous sweep of $N_2$. The acidity was trapped in the water remaining in the distillation tube. This eliminated the neutralization of LiOH or LiCN to $Li_2SO_4$ by the $H_2SO_4$ in the HCN and thereby permitted use of the LiCN catalyst in a mole ratio of 0.005:1.00 Li:HCN.

IPH was charged and heated to ~80° C. and the catalyst was prepared and added as described in Example 1. The HCN pump was started while simultaneously increasing the set-point of the controller to 110° C. The reaction temperature rose to 110° C. within 10-15 minutes. After the end of the HCN feed, the IPN solution was held at 110° C. for 30 minutes. The temperature was then raised to 140° C. in an effort to determine whether the HCN concentration could be forced to <10 ppm by such a treatment, and the batch was held for 3 hours. At the end of the 3 hours, the IPN solution was cooled to 85° C., acidified with D,L malic acid, and $N_2$ sparged for an additional 2.5 hours. It was then cooled to 80° C. and filtered. The concentration of HCN in the filtered product was 4 ppm. The yield of IPN calculated from HPLC analysis was 99+%.

EXAMPLE 3

The apparatus of Example 2 was used. Isophorone having a 5% pH of 5.28 and an acidity of 0.0015 meq $H^+/g$ was neutralized by addition of 0.80 grams LiOH•$H_2O$ in methanol, thereby producing a 5% pH of 8.41. The HCN was not distilled, thus, to be certain that the Li catalyst was present in sufficient excess over the acidity in the HCN, a mole ratio of 0.0075M Li:1.00M HCN was used. The neutralized IPH was heated to 80° C., LiCN in methanol was added, and HCN addition was immediately started. The temperature was linearly ramped to 110° C. over 15 minutes and then held at 110° C. The time of addition was 63 minutes. The batch was held at 110° C. for an additional 30 minutes. The free HCN concentration was 85 ppm. The conversion was 98% and the impurity level was 1.08%.

EXAMPLE 4

The apparatus of Example 2 was used, with the addition of a Harvard Pump Speed Modulator which was interfaced with the Harvard syringe pump.

Isophorone having a 5% pH of 4.83 and an acidity of $3.2 \times 10^{-3}$ meq $H^+/g$ was neutralized with 1.4 grams of 5.0% methanolic LiOH, thereby raising the 5% pH to 7.48. This IPH was equilibrated at 80° C., the methanolic LiOH or LiCN catalyst was added, then the HCN feed was immediately started. Samples were taken during the run and titrated for cyanide. When these results were in hand, a new temperature/feed rate profile was calculated based upon the cyanide analyses and the experiment was then repeated using the new profile. This was continued over several experiments, each time attempting to approach a constant and low concentration of free HCN throughout the course of each reaction. The results are summarized in Table II.

TABLE II
EXPERIMENTS USING NON-LINEAR TEMPERATURE AND HCN FEED RATE PROFILES
Catalyst is LiCN (methanol + LiOH.H20 + HCN)

|  | L/N 1 | | L/N 2 | | L/N 3 | | L/N 4 | |
|---|---|---|---|---|---|---|---|---|
| Mole Ratio Li:HCN = 1.000 | .0075 | | .0075 | | .0075 | | .0080 | |
|  | Minutes | ppm HCN | Minutes | ppm HCN | Minutes | ppm HCN | Minutes | ppm HCN |
| Free HCN analyses during HCN feed | 10 | 321 | 9 | 509 | 9 | 3938 | 9 | 1908 |
|  | 18 | 1928 | 18 | 3201 | 18 | 3856 | 18 | 4274 |
|  | 27 | 3495 | 27 | 6642 | 27 | 5503 | 27 | 3406 |
|  | 36 | 4146 | 36 | 5835 | 36 | 3754 | 36 | 5135 |
|  | 45 | 6692 | 45* | 9663 | 45 | 5006 | 45 | 4603 |
|  | 55 | 6824 | | | 57* | 5266 | 48 | |
|  | 63 | 14319 | | | | | | |
|  | 72 | 5735 | | | | | | |
|  | 81* | 5682* | | | | | | |
| During hold @ 110° C. | | | | | 15 | 2646 | 15 | 100 |
|  | 30 | 4252 | | | 30 | 2024 | 30 | 82 |
|  | | | 60 | 7564 | 60 | 755 | | |
| Final crude IPN/IPH solution | | | | | | | | |
| % IPN by G.C. | 39.4% | | | | 48.1% | | 48.0% | |
| % IPH by G.C. | 60.0% | | | | 51.5% | | 50.8% | |
| % Impurities by G.C. | 0.0% | | | | 0.0% | | 0.0% | |
| % IPN Yield by G.C. | 74.3% | | | | 90.8% | | 90.6% | |
| % IPN by L.C. | | | | | | | 48.1% | |
| % IPH by L.C. | | | | | | | 47.7% | |
| % IPN Yield by L.C. | | | | | | | 90.8% | |

|  | L/N 5 | | L/N 6 | | L/N 7 | | L/N 8 | |
|---|---|---|---|---|---|---|---|---|
| Mole Ratio Li:HCN = 1.000 | .0080 | | .0080 | | .0080 | | .0080 | |
|  | Minutes | ppm HCN | Minutes | ppm HCN | Minutes | ppm HCN | Minutes | ppm HCN |
| Free HCN analyses during HCN feed | 9 | 1421 | 9 | 2853 | 9 | 858 | 9 | 3405 |
|  | 18 | 4835 | 18 | 1440 | 18 | 312 | 18 | 6049 |
|  | 27 | 6989 | 27 | 598 | 27 | 401 | 27 | 8088 |
|  | 36 | 6126 | 36 | 1252 | 36 | 437 | 36 | 8692 |
|  | 45 | 7171 | 45 | 1197 | 45 | 385 | 45 | 9026 |
|  | 58* | 3984 | 54 | 1579 | 58* | 256 | 54 | 7778 |
|  | | | 67* | 1620 | | | 63 | 6421 |
|  | | | | | | | 72 | 5356 |
|  | | | | | | | 81 | 3688 |
|  | | | | | | | 90 | 3129 |
|  | | | | | | | 99 | 3122 |
|  | | | | | | | 108* | 2565 |
| During hold @ 110° C. | 15 | 80 | 15 | 98 | 15 | 208 | | |
|  | 30 | 57 | 30 | 60 | 30 | | | |
|  | | | | | | | 60 | 106 |
| Final crude IPN/IPH solution | | | | | | | | |
| % IPN by G.C. | 51.1% | | 52.4% | | 51.1% | | 52.4% | |
| % IPH by G.C. | 48.3% | | 46.3% | | 44.2% | | 46.3% | |

TABLE II-continued

EXPERIMENTS USING NON-LINEAR TEMPERATURE AND HCN FEED RATE PROFILES
Catalyst is LiCN (methanol + LiOH.H20 + HCN)

| % Impurities by G.C. | 0.0% | 0.8% | 1.3% | 0.8% |
|---|---|---|---|---|
| % IPN Yield by G.C. | 96.4% | 98.9% | 96.7% | 98.9% |
| % IPN by L.C. | 51.2% | 50.8% | | 50.8% |
| % IPH by L.C. | 44.9% | 42.4% | | 42.4% |
| % IPN Yield by L.C. | 96.6% | 95.9% | | 95.9% |

Note: High quality U.C. isophorone was not available for these runs.
*End of HCN feed

EXAMPLE 5

The following runs were carried out to compare a reaction scheme whereby a programmed HCN feed rate and temperature ramp were used to one where the heat of reaction was employed to ramp the temperature while the HCN feed rate was maintained constant.

The first and third batches were identical. Isophorone was charged to a 200 gallon reactor and heated to 80° C. A solution of 5% LiOH in $CH_3OH$ was charged and the HCN feed was promptly initiated. The reaction exotherm was allowed to raise the batch temperature from 80° C. to 110° C., and then the temperature was maintained at 110° C. for the remainder of the HCN feed. After the HCN feed, the catalyst was neutralized with a 10% excess of freshly prepared 30% malic acid in $CH_3OH$. The neutralized catalyst was removed by filtration and the batch was vacuum stripped free of isophorone.

Figure 2A:
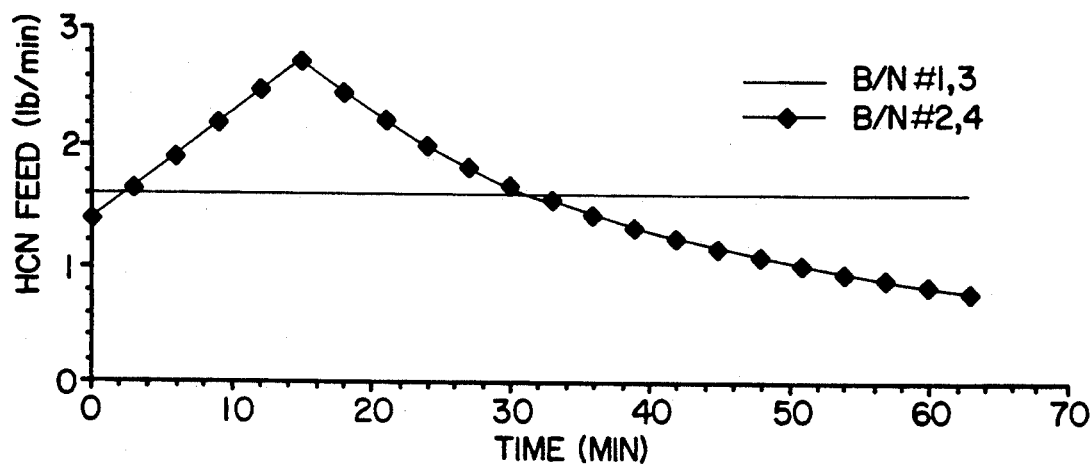
FIG. 2a is a graph showing the feed rate of HCN to the reaction system in accordance with one embodiment of the present invention.
Figure 2B:
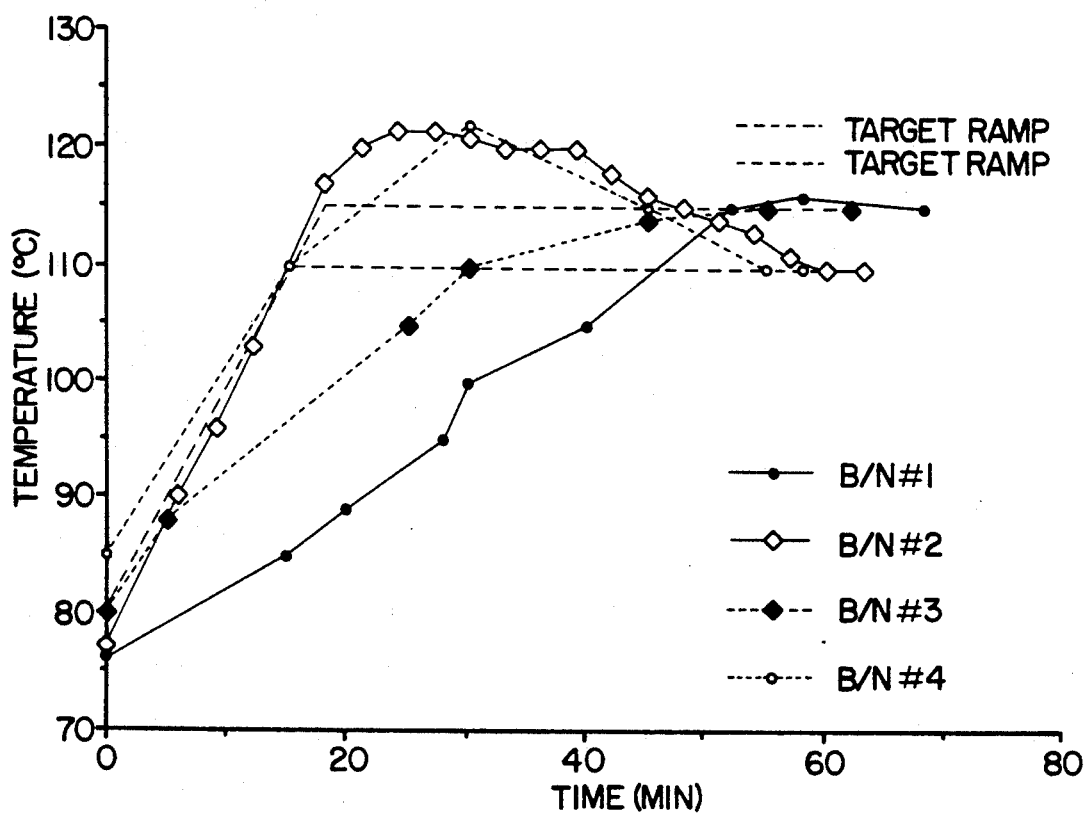
FIG. 2b is a graph of Temperature vs. Time.

In the second and fourth batches, the HCN feed rate was not linear. Instead, the feed rate was varied with time as illustrated in FIG. 2. Results are shown in Table III.

TABLE III

| | Batch No. | | | |
|---|---|---|---|---|
| | 1 | 2 | 3 | 4 |
| IPN %[5] | 97.8 | 90.1 | 97.5 | 96.1 |
| IPH %[5] | 1.1 | 1.1 | 0.3 | 0.9 |
| Li, ppm[1] | 7 | 10 | 18 | 9 |
| Cyanide, ppm[2] | Nil | Nil | Nil | Nil |
| pH (5% sol.)[3] | 4.7 | 5.18 | 4.93 | 4.79 |
| GC Impurities[4] | 1.1 | 8.8 | 2.2 | 3.0 |
| Starting IPH, % | 99.7 | 99.7 | 99.7 | 99.7 |

[1] Li by AA
[2] Borate Buffer titration
[3] Apparent pH, in 50/50 IPA/$H_2O$
[4] Other than IPH, includes dimers
[5] By GC (internal standard)

In batch 1, a constant HCN feed rate was employed and the reaction exotherm was allowed to raise the reaction temperature from 80° to 110° C. Approximately 40 minutes were required to achieve the desired temperature, since the reactor jacket contained hot water (60° C.) which acted as an energy sink. The results of this batch were excellent.

Batch 2 employed a programmed HCN feed rate and temperature ramp. The programmed feed rate was very accurately maintained but the temperature ramp was not. In the early stages, the temperature lagged behind the programmed temperature and a sizeable exotherm occurred once the batch reached the target temperature. The batch remained above the 110°-115° C. target temperature range for 20 minutes. The results were poor.

Batch 3 was a replicate of batch 1, except that the reactor jacket was empty during the temperature ramp portion of the HCN feed. The reaction exotherm raised the batch temperature from 80° to 110° C. in 20 minutes. The results were excellent.

Batch 4 was a repeat of the programmed feed of batch 2, except that batch 4 was aggressively steam heated at the start of the HCN feed so that the temperature program could be maintained. However, an exotherm still resulted which caused the batch temperature to exceed 115° C. The results of this batch were superior to batch 2, but inferior to batches 1 and 3.

EXAMPLE 6

The apparatus of Example 2 was used. The isophorone employed had no titratable acidity. The catalyst in each batch was added to 558.4 grams of IPH at 80° C. and then immediately and simultaneously the HCN addition was begun at a linear rate over 60 minutes using a linear temperature ramp of 80° C. to 110° C. over 15 minutes followed by holding at 110° C. for the balance of the feed (total 54.1 grams HCN) plus a 30 minute hold period during which the residual free HCN dropped to ~100 ppm. The following catalysts were used:

| Batch No. | Catalyst | Mole Ratio Li:1.00 HCN |
|---|---|---|
| 1 | LiCN, 4% in MeOH | 0.0050 |
| 2 | LiCN, 4% in MeOH | 0.0075 |
| 3 | LiOH, 8% in $H_2O$ | 0.0075 |
| 4 | LiOH.$H_2O$, solid | 0.0075 |

The results for these batches are summarized in Table IV. The analytical and yield data are for the crude IPN/IPH solution after a hold at 110° C. and cooling to 50° C.

TABLE IV

Experiments using high quality isophorone
Comparison of lithium catalysts

| | L/N | | | |
|---|---|---|---|---|
| | 1 | 2 | 3 | 4 |
| Catalyst | LiCN | LiCN | LiOH | LiOH.H2O |
| Form | 4% in MeOH | 4% in MeOH | 8% in H2O | solid |
| Mole Ratio Li:HCN (HCN = 1.00) | 0.005 | 0.075 | 0.075 | 0.075 |
| Minutes hold @ 110° C./ppm HCN | 30/4400 ppm | 30/129 ppm | 30/12950 ppm<br>90/10650 ppm<br>180/9665 ppm | 30/278 ppm<br>90/211 |

GC based data: new method w. int. std.

TABLE IV-continued

Experiments using high quality isophorone
Comparison of lithium catalysts

|  | L/N | | | |
|---|---|---|---|---|
|  | 1 | 2 | 3 | 4 |
| % IPN | 52.4% | 56.8% | 49.8% | 58.5% |
| % IPH | 46.4% | 41.4% | 48.8% | 43.9% |
| % Impurities | 0.1% | 0.3% | 0.0% | 0.0% |
| % Yield | 98.3% | 99.0% | 94.0% | 99.0% |
| Appearance of Final Solution | clear, dark yellow | clear, light yellow | slightly turbid, yellow-red | clear, yellow-red |

Note: Analytical and yield data are for the crude INPH/IPH solution after a hold @ 110° C. and cooled to 50° C.

EXAMPLE 7

The apparatus of Example 1 was used. 0.11 grams of water/M IPH was added to the IPH to simulate a line flush in a plant-scale process. The HCN feed was begun, followed immediately by the addition of 5% LiOH•H$_2$O/MeOH catalyst. The crude product was treated with 30% aqueous malic acid and then nitrogen sparged at 120° C. to remove the water. The batch was cooled to approximately 80° C. and filtered through a medium porosity filter paper. The Li$_2$ malate precipitate was easily removed by this filtration, and the filtrate was analyzed. This experiment was replicated, and the data generated are illustrated in Table V.

TABLE V

|  | 1 | 2 |
|---|---|---|
| ppm HCN before acidification | 133 | 106 |
| ppm HCN in filtrate | 64 |  |
| ppm Li | 0.88 | 0.96 |
| % H$_2$O by K.F. Titrn. | 0.04% | 0.16% |
| *Conversion | 99+% | 98.5% |
| % IPN | 53.5% | 52.5% |
| % Yield of IPN from HCN | 99.4% | 98.5% |
| **Impurities by G.C. | 2.22% | 6.40% |

*Conversion: % of HCN consumed; i.e., % of HCN converted to organic cyanide derivatives.
**Impurities: % of area of G.C. peaks not attributable to IPN ÷ total area.

EXAMPLE 8

Example 7 was repeated except that solid LiOH•H$_2$O (0.08 M/M HCN) was used as the catalyst, solid malic acid (0.6 M/M Li) was used for acidification, and the 0.11 g of water was eliminated. The run was carried out in duplicate. The amount of free HCN before acidification was 39 ppm and 109 ppm, demonstrating that reaction is complete when solid catalyst is used. The Li content of the filtrates was 0.97 ppm.

EXAMPLE 9

Example 8 was repeated using solid LiOH•H$_2$O as catalyst. The batch was split into several portions and acidified with various amounts of solid malic acid, as set forth in Table VI. The filtrates were analyzed for lithium. The data confirm that a mole ratio of malic acid:Li of 0.50:1.00 is sufficient for nearly complete removal of the catalyst.

TABLE VI

| Mole Ratio Malic Acid:Li | 5% pH | ppm Li in Filtrate |
|---|---|---|
| 0.50:1.00 | 5.77 | 1.48 |
| 0.55:1.00 | 5.74 | 1.76 |
| 0.60:1.00 | 5.41 | 1.97 |
| 0.65:1.00 | 4.88 | 2.38 |
| 0.70:1.00 | 4.73 | 1.71 |

EXAMPLE 10

Example 8 was repeated, except that the IPH used analyzed as 91.04% IPH and 4.89% impurities by G.C. Consequently, an increased charge of IPH was used to account for the low IPH assay. The reaction proceeded normally, with an HCN conversion of 99+%.

What is claimed is:

1. A process for the preparation of isophorone nitrile, comprising:
   a. reacting isophorone with hydrogen cyanide in the presence of a catalytic amount of LiCN at a reaction temperature from about 80° C. to 115° C. upon catalyst addition, while maintaining the hydrogen cyanide concentration sufficient to prevent the generation of free LiOH;
   b. acidifying the resulting solution with a polyacidic acid selected from the group consisting of malic (hydroxysuccinic) acid, oxalic acid, sulfuric acid and phosphoric acid to precipitate the lithium salt of said acid; and
   c. separating the resultant mother liquor from said precipitate.

2. The process of claim 1 wherein said hydrogen cyanide concentration is maintained in the range of about 200 to about 4000 ppm.

3. The process of claim 1 wherein said acid is malic acid.

4. The process of claim 1 wherein said isophorone is distilled prior to step a.

5. The process of claim 1 further comprising vacuum stripping said mother liquor.

6. The process of claim 1 wherein said mother liquor is separated from said precipitate by filtering said precipitate.

7. The process of claim 1 wherein the mole ratio of lithium to total hydrogen cyanide to be added is less than 0.01:1.

8. The process of claim 1 wherein the acidity is removed from said hydrogen cyanide prior to the reaction.

9. The process of claim 8 wherein the mole ratio of lithium to total hydrogen cyanide to be added is about 0.005:1.

10. The process of claim 1, wherein said catalytic amount of LiCN is derived from a lithium source selected from the group consisting of solid lithium hydroxide, solid lithium hydroxide mono-hydrate, and solutions of lithium hydroxide.

11. The process of claim 10, wherein said solutions of lithium hydroxide comprise lithium hydroxide dissolved in methanol.

12. A process for the preparation of isophorone nitrile, comprising:
   a. introducing isophorone into a reaction vessel;

b. initiating the introduction of hydrogen cyanide into said reaction vessel;

c. introducing a lithium source selected from the group consisting of solid lithium hydroxide, solid lithium hydroxide mono-hydrate, and solutions of lithium hydroxide into said reaction vessel to form a catalytic amount of LiCN; and d. continuing the feed of hydrogen cyanide into said reaction vessel at a rate sufficient to prevent the generation of free LiOH, while ramping the reaction temperature to about 110° C. and maintaining that temperature during the reaction.

13. The process of claim 12, wherein the acidity of said isophorone is neutralized prior to its reaction with said hydrogen cyanide.

14. The process of claim 12, wherein said reaction temperature is linearly ramped to about 110° C.

15. The process of claim 12, wherein the reaction exotherm is allowed to ramp said reaction temperature to about 110° C.

16. The process of claim 12, wherein the concentration of said hydrogen cyanide is maintained in the range of about 200 to about 4000 ppm during the reaction.

17. The process of claim 12, further comprising acidifying the reaction product with a polyacid selected from the group consisting of malic (hydroxysuccinic) acid, oxalic acid, sulfuric acid and phosphoric acid to precipitate the lithium salt of said acid.

18. The process of claim 17, wherein said polyacidic acid is malic acid.

19. The process of claim 17, further comprising separating said precipitate from the resultant mother liquor.

20. The process of claim 19 wherein said precipitate is removed by filtration.

21. The process of claim 19, further comprising vacuum stripping said mother liquor.

22. The process of claim 12, wherein the mole ratio of lithium to total hydrogen cyanide to be added is less than 0.01:1.

23. The process of claim 12, wherein the mole ratio of lithium to total hydrogen cyanide to be added is about 0.005:1.

24. The process of claim 12, wherein said hydrogen cyanide is distilled prior to feeding the same into said reaction vessel.

25. The process of claim 12, further comprising heating said isophorone to about 80° C. prior to introduction of said catalyst.

26. The process of claim 12, wherein said solutions of lithium hydroxide comprise lithium hydroxide dissolved in methanol.

27. The process according to claim 10, wherein the solvent for lithium hydroxide is an organic solvent selected from the group consisting of dioxane, methanol and ethanol.

28. The process according to claim 12, wherein the solvent for lithium hydroxide is an organic solvent selected from the group consisting of dioxane, methanol and ethanol.

* * * * *